United States Patent
Ha et al.

(10) Patent No.: US 12,204,372 B2
(45) Date of Patent: Jan. 21, 2025

(54) ELECTRONIC DEVICE INCLUDING CONDUCTIVE KEY BUTTON

(71) Applicant: Samsung Electronics Co., Ltd., Suwon-si (KR)

(72) Inventors: Youngsoo Ha, Suwon-si (KR); Yoonhee Lee, Suwon-si (KR); Hangyu Hwang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 18/172,667

(22) Filed: Feb. 22, 2023

(65) Prior Publication Data

US 2023/0367367 A1     Nov. 16, 2023

Related U.S. Application Data

(63) Continuation of application No. PCT/KR2023/000951, filed on Jan. 19, 2023.

(30) Foreign Application Priority Data

May 13, 2022 (KR) .................. 10-2022-0059138
Jun. 8, 2022 (KR) .................. 10-2022-0069642

(51) Int. Cl.
*G06F 1/16*     (2006.01)
*G06F 3/01*     (2006.01)
(Continued)

(52) U.S. Cl.
CPC .............. *G06F 1/163* (2013.01); *G06F 3/011* (2013.01); *G06F 3/02* (2013.01); *G06V 10/17* (2022.01); *G06V 40/1329* (2022.01)

(58) Field of Classification Search
CPC .......... G06F 3/048; G06F 3/01; G06F 3/0481; G06F 3/0488; G06F 3/03; G06F 3/0362
See application file for complete search history.

(56) References Cited

U.S. PATENT DOCUMENTS 6,372,598 B2    4/2002   Kang et al.
10,153,203 B2   12/2018   Wang et al.
(Continued)

FOREIGN PATENT DOCUMENTS

CN     201750462 U    2/2011
CN     204423314 U    6/2015
(Continued)

OTHER PUBLICATIONS

International Search Report and Written Opinion dated Apr. 5, 2023, issued in International Patent Application No. PCT/KR2023/000951.

*Primary Examiner* — Michael A Faragalla
(74) *Attorney, Agent, or Firm* — Jefferson IP Law, LLP

(57) ABSTRACT

According to an embodiment, an electronic device includes a housing providing an inner space, a sensor disposed in the inner space, and a key button including an electrode electrically connected to the sensor and configured to obtain biometric information through a contact with an external object through the sensor, wherein the key button includes a metal layer, a deposited layer including a hole connected to a part of the metal layer and disposed on the metal layer, and a conductive material disposed in the hole and contact with the metal layer exposed through the hole, wherein a diameter of one side of the hole facing an outside is greater than a thickness of the deposited layer.

18 Claims, 9 Drawing Sheets

(51) Int. Cl.
*G06F 3/02* (2006.01)
*G06V 10/10* (2022.01)
*G06V 40/13* (2022.01)

(56) References Cited

U.S. PATENT DOCUMENTS

| | | | |
|---|---|---|---|
| 10,614,202 | B2 | 4/2020 | Song et al. |
| 11,036,318 | B2 | 6/2021 | Bokma et al. |
| 11,181,863 | B2 | 11/2021 | Ely et al. |
| 11,194,299 | B1 * | 12/2021 | Taylor ................. G06F 3/016 |
| 2017/0322647 | A1 * | 11/2017 | Katsuhara ............... G06F 3/02 |
| 2019/0025940 | A1 * | 1/2019 | Shim .................. G06F 3/0362 |
| 2019/0384434 | A1 * | 12/2019 | Li ........................ G06F 3/0412 |
| 2021/0204876 | A1 | 7/2021 | Pandya et al. |
| 2022/0164562 | A1 * | 5/2022 | Pan ..................... G06V 40/13 |
| 2022/0303372 | A1 | 9/2022 | Choi et al. |

FOREIGN PATENT DOCUMENTS

| | | |
|---|---|---|
| KR | 10-0319888 B1 | 1/2002 |
| KR | 10-0663892 B1 | 1/2007 |
| KR | 10-2007-0058057 A | 6/2007 |
| KR | 10-1206918 B1 | 11/2012 |
| KR | 10-2015-0131844 A | 11/2015 |
| KR | 10-2022-0129822 A | 9/2022 |

\* cited by examiner

ELECTRONIC DEVICE INCLUDING CONDUCTIVE KEY BUTTON

CROSS-REFERENCE TO RELATED APPLICATION(S)

This application is a continuation application, claiming priority under § 365(c), of an International application No. PCT/KR2023/000951, filed on Jan. 19, 2023, which is based on and claims the benefit of a Korean patent application number 10-2022-0059138, filed on May 13, 2022, in the Korean Intellectual Property Office, and of a Korean patent application number 10-2022-0069642, filed on Jun. 8, 2022, in the Korean Intellectual Property Office, the disclosure of each of which is incorporated by reference herein in its entirety.

TECHNICAL FIELD

Embodiments to be described later relate to an electronic device including a conductive key button.

BACKGROUND ART

A portable electronic device such as a smart phone, a smart watch, or a watch phone may comprise a key that is exposed to the outside. The key button of the electronic device may provide a user input. The key of the electronic device may provide not only the user input but may additionally provide other functions.

DISCLOSURE

Technical Problem

A portable electronic device may comprise a key button exposed to the outside of a housing. The key button exposed to the outside may comprise an additional color layer for the color and unity of the housing.

The key button having the same color as the color of the housing may have a thick color layer. Due to the color layer, it may be difficult to implement an additional function assigned to the key button. A plan is needed to perform additional functions.

The technical problems to be achieved in this document are not limited to those described above, and other technical problems not mentioned herein will be clearly understood by those having ordinary knowledge in the art to which the present disclosure belongs, from the following description.

Technical Solution

According to an embodiment, an electronic device may comprise a housing including a front surface, a rear surface, and a side surface disposed between the front surface and the rear surface, and providing an inner space surrounded by the front surface, the rear surface, and the side surface, a sensor disposed in the inner space, and a key button including an electrode electrically connected to the sensor, and configured to obtain biometric information through a contact with an external object through the sensor, and at least partially inserted into an opening formed on the side surface, wherein the key button includes a metal layer, a deposited layer including a hole exposing a portion of the metal layer and disposed on the metal layer, and a conductive material disposed in the hole and in contact with the metal layer exposed through the hole, wherein a diameter of a one side of the hole facing an outside may be greater than a thickness of the deposited layer.

An electronic device according to an embodiment may comprise a housing including a front surface, a rear surface contact with a part of a user's body when the electronic device is worn by the user, and a side surface disposed between the front surface and the rear surface, and providing an inner space surrounded by the front surface, the rear surface, and the side surface, a display disposed on the front surface, a strap surrounding the part of the user's body when the electronic device is worn by the user and is rotatable with respect to the housing, a sensor disposed in the inner space, an at least one key button including a first electrode electrically connected to the sensor and configured to obtain biometric information through contact with an external object through the sensor, and at least partially inserted into an opening formed on the side surface, and a second electrode disposed on the rear surface, wherein the at least one key button includes a metal layer having a groove, a deposited layer including a hole connected to the groove and disposed on the metal layer, a conductive material disposed in the groove and the hole and contact with the metal layer exposed through the groove, and processor, wherein a diameter of a one side of the hole facing an outside may be greater than a thickness of the deposited layer and wherein the processor is configured to obtain data related to the biometric information based on sensing data obtained through the sensor electrically connected to the first electrode and the second electrode.

Advantageous Effects

The electronic device according to an embodiment can transmit microcurrent generated by an external object to an electronic component inside the electronic device by including a key button including a conductive material.

The key button included in the electronic device according to an embodiment can reduce a color heterogeneity with a housing of the electronic device by including a deposited layer.

The effects that can be obtained from the present disclosure are not limited to those described above, and any other effects not mentioned herein will be clearly understood by those having ordinary knowledge in the art to which the present disclosure belongs, from the following description.

MODE FOR INVENTION

Figure 1:
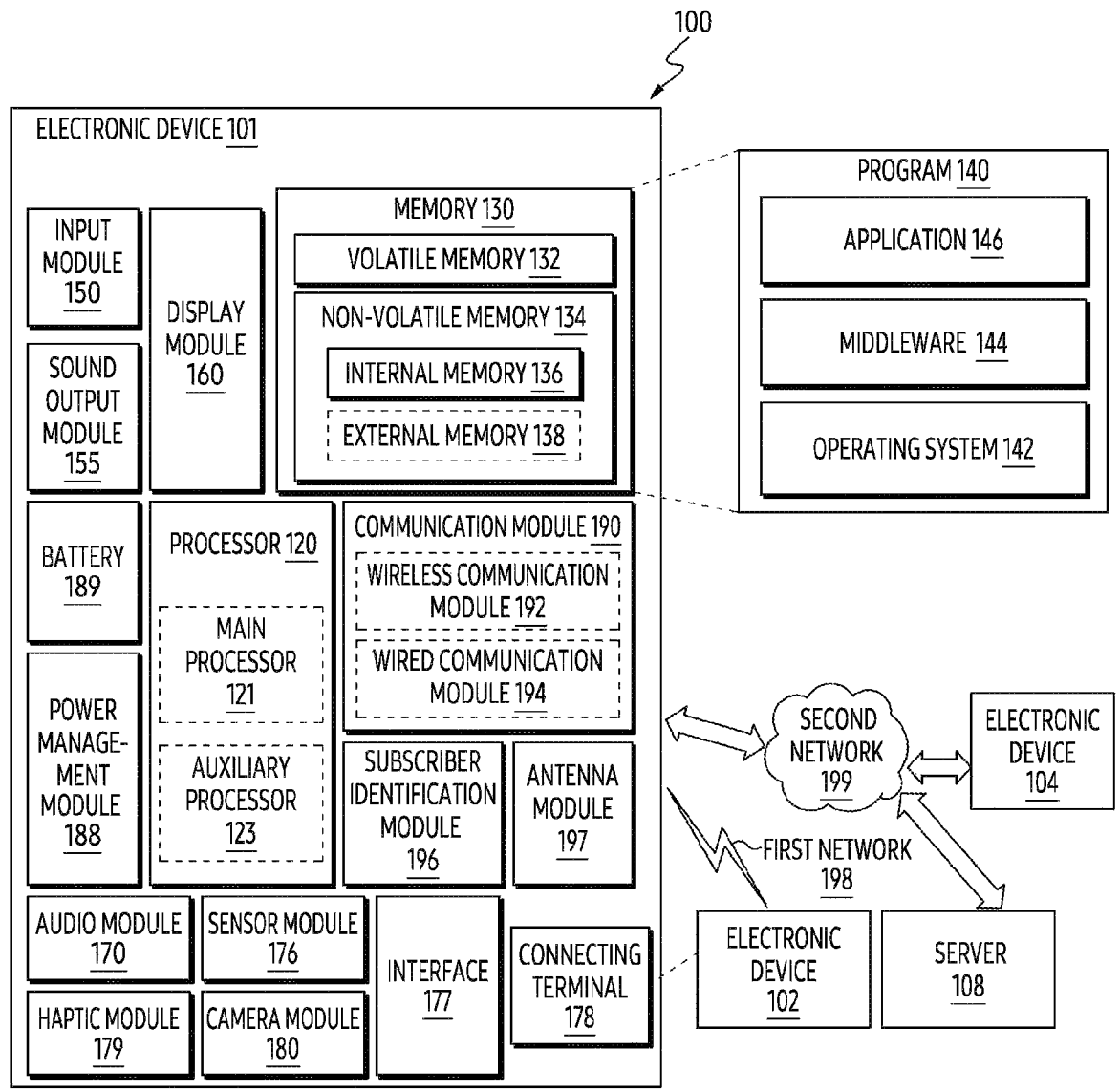
FIG. 1 is a block diagram of an electronic device in a network environment according to various embodiments.

FIG. 1 is a block diagram illustrating an electronic device in a network environment according to various embodiments.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
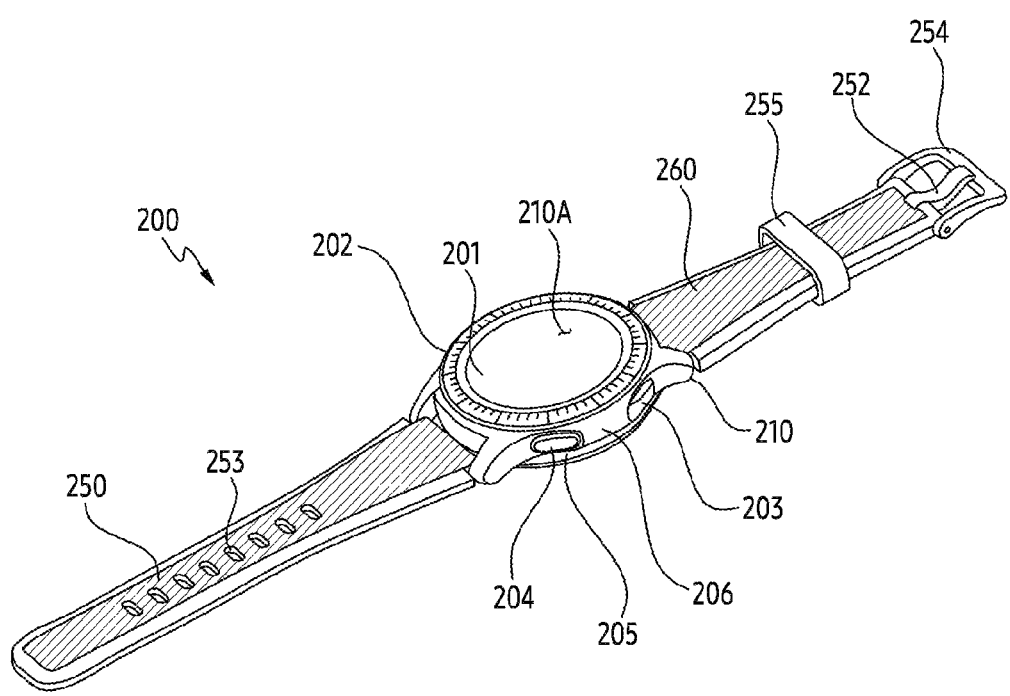
FIG. 2 is a perspective view of a front surface of an electronic device according to an embodiment.

FIG. 2 is a perspective view of a front surface of an electronic device according to an embodiment.

Figure 3:
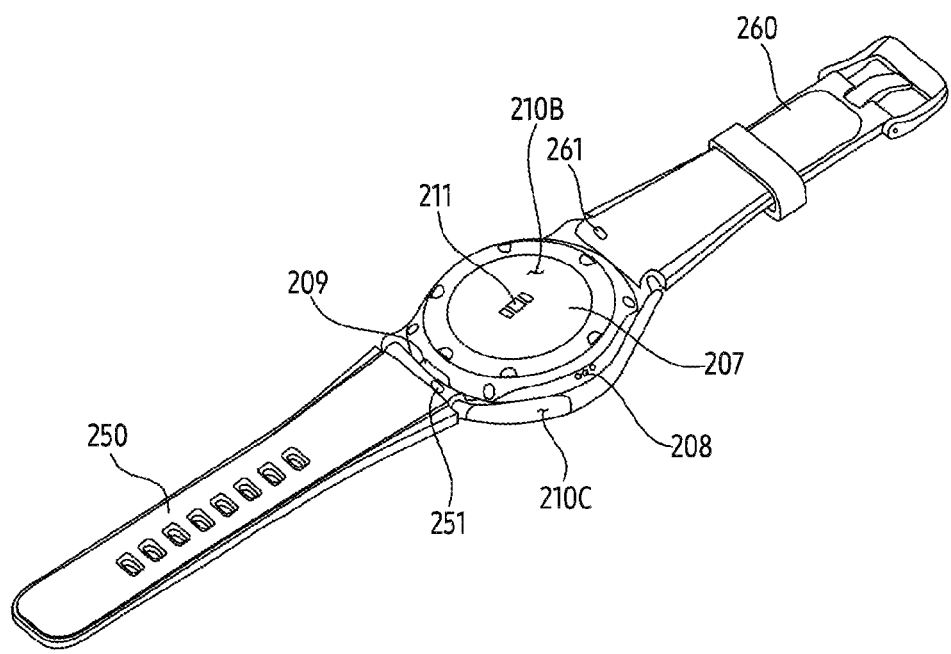
FIG. 3 is a perspective view of a rear surface of the electronic device in FIG. 2.

FIG. 3 is a perspective view of a rear surface of the electronic device in FIG. 2.

Referring to FIGS. 2 and 3, an electronic device 200 according to an embodiment may include a housing 210 including a front surface 210A, a rear surface 210B, and a side surface 210C surrounding the space between the front surface 210A and the rear surface 210B and binding members 250 and 260 connected to at least a part of the housing 210 and configured to detachably attach the electronic device 200 to a part of the user's body (e.g., wrist, ankle, etc.). In another embodiment (not illustrated), the housing may also refer to a structure that forms at least a part of the front surface 210A, the rear surface 210B, and the side surface 210C of FIG. 2. According to an embodiment, at least a part of the front surface 210A may be implemented by a substantially transparent front plate 201 (e.g., glass plate or polymer plate including various coating layers). The rear surface 210B may be implemented by a substantially opaque rear plate 207. The rear plate 207 may be made of, for example, coated or colored glass, ceramic, polymer, metal (e.g., aluminum, stainless steel (STS), or magnesium), or a combination of at least two of the materials. The side surface 210C may be coupled to the front plate 201 and the rear plate 207, and may be implemented by a side bezel structure 206 including metal and/or polymer. In some embodiments, the rear plate 207 and the side bezel structure 206 may be integrally formed and may include the same material (e.g., metal material such as aluminum). The binding members 250 and 260 may be made of various materials and may be made in various shapes. The binding members 250 and 260 may be made of woven fabric, leather, rubber, urethane, metal, ceramic, or a combination of at least two of the materials.

According to an embodiment, the electronic device 200 may include at least one of a display 220 (see FIG. 3), an audio module 205 and 208, a sensor module 211, a key input device 202, 203 and 204, and a connector hole 209. In some embodiments, the electronic device 200 may omit at least one of the components (e.g., the key input devices 202, 203 and 204, the connector hole 209, or the sensor module 211) or may further include another component.

The display 220 may be exposed, for example, through a substantial portion of the front plate 201. The shape of the display 220 may correspond to the shape of the front plate 201, such as circular (shown in FIG. 2), oval, or polygonal. The display 220 may be coupled to or adjacent to a touch sensing circuit, a pressure sensor capable of measuring the strength (pressure) of touches, and/or a fingerprint sensor.

The audio modules 205 and 208 may include a microphone hole 205 and a speaker hole 208, a microphone for obtaining external sound may be disposed inside the microphone hole 205, and in some embodiments, a plurality of microphones may be disposed to detect the direction of the sound. The speaker hole 208 may be used with an external speaker and a receiver for phone calls. In some embodiments, the speaker hole 208 and the microphone hole 205 may be implemented as a single hole, or a speaker (e.g., piezo speaker) may be included without the speaker hole 208.

The sensor module 211 may generate electrical signal(s) or data value(s) corresponding to internal operating state(s) of the electronic device 200 or external environmental state(s). The sensor module 211 may include, for example, a biometric sensor module 211 (e.g., heart-rate monitor (HRM) sensor) disposed on the rear surface 210B of the housing 210. The electronic device 200 may further include at least one sensor module not shown, such as a gesture sensor, a gyro sensor, a pressure sensor, a magnetic sensor, an acceleration sensor, a grip sensor, a color sensor, an infrared sensor, a biometric sensor, a humidity sensor, and/or an illumination sensor.

The key input devices 202, 203, and 204 may include a wheel key 202 disposed on the front surface 210A of the housing 210 and rotatable in at least one direction, and/or key buttons 203 and 204 disposed on the side surface 210C of the housing 210. The wheel key may have a shape corresponding to the shape of the front plate 201. In another embodiment, the electronic device 200 may not include some or all of the above-described key input devices 202, 203, and 204, and the not included key input devices 202, 203, and 204 may be implemented in other forms such as soft keys on the display 220.

The connector hole 209 may accommodate a connector (e.g., USB connector) for transmitting and receiving power and/or data to and from external electronic devices and may include another connector hole (not illustrated) capable of accommodating a connector for transmitting and receiving audio signals to and from an external electronic device. The electronic device 200 may further include, for example, a connector cover (not illustrated) that covers at least a part of the connector hole 209 and blocks the inflow of external foreign material into the connector hole.

The binding members 250 and 260 may be detachably attached to at least a part of the housing 210 using locking members 251, 261. The binding members 250 and 260 may include one or more of a fixing member 252, a fixing member fastening hole 253, a band guide member 254, and a band fixing ring 255.

The fixing member 252 may be configured to fix the housing 210 and the binding members 250 and 260 to a part of the user's body (e.g., wrist, ankle, etc.). The fixing member fastening hole 253 may correspond to the fixing member 252 to fix the housing 210 and the binding members 250 and 260 to the part of the user's body. The band guide member 254 may be configured to limit movement range of the fixing member 252 when the fixing member 252 is fastened to the fixing member fastening hole 253, so that the binding members 250 and 260 are attached to be in close contact with the part of the user's body. The band fixing ring 255 may limit the range of movement of the fixing members 250 and 260 when the fixing member 252 and the fixing member fastening hole 253 are fastened.

Figure 4:
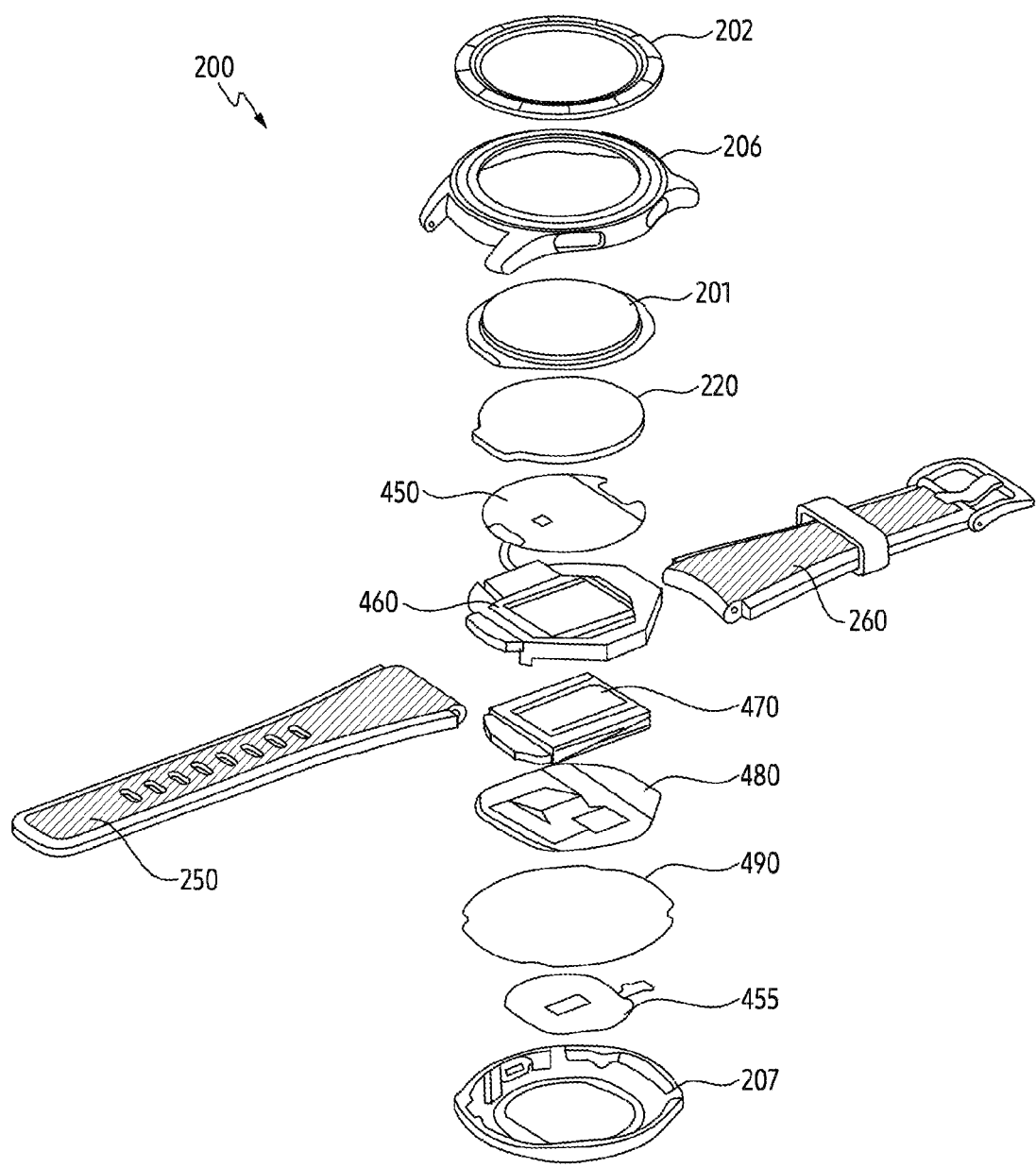
FIG. 4 is an exploded perspective view of the electronic device in FIG. 2.

FIG. 4 is an exploded perspective view of the electronic device in FIG. 2.

Referring to FIG. 4, an electronic device 200 may include a side bezel structure 206, a wheel key 202, a front plate 201, a display 220, a first antenna 450, a second antenna 455, a support member 460 (e.g., bracket), a battery 470, a printed circuit board 480, a sealing member 490, a rear plate 207, and binding members 250 and 260. At least one of the components of the electronic device 200 may be the same as or similar to at least one of the components of the electronic device 200 of FIG. 2, or 3, and repeated description thereof will be omitted. The support member 460 may be disposed inside the electronic device 200 to be connected to the side bezel structure 206 or may be integrated with the side bezel structure 206. The support member 460 may be made of, for example, metal material and/or non-metal (e.g., polymer) material. The display 220 may be coupled to one surface of the support member 460, and the printed circuit board 480 may be coupled to the other surface of the support member 460. A processor, a memory, and/or an interface may be mounted on the printed circuit board 480. The processor may include, for example, one or more of a central processing unit, an application processor, a graphic processing unit (GPU), an application processor sensor processor, or a communication processor.

The memory may include, for example, a volatile memory or a nonvolatile memory. The interface may include, for example, a high definition multimedia interface (HDMI), a universal serial bus (USB) interface, an SD card interface, and/or an audio interface. The interface may electrically or physically connect the electronic device 200 to an external electronic device, for example, and may include a USB connector, an SD card/MMC connector, or an audio connector.

The battery 470 is a device for supplying power to at least one component of the electronic device 200, and may include, for example, a non-rechargeable primary battery, a rechargeable secondary battery, or a fuel battery. At least a part of the battery 470 may be disposed on substantially the same plane as, for example, the printed circuit board 480. The battery 470 may be integrally disposed inside the electronic device 200 or may be detachably coupled to the electronic device 200.

The first antenna 450 may be disposed between the display 220 and the support member 460. The first antenna 450 may include, for example, a near field communication (NFC) antenna, a wireless charging antenna, and/or a magnetic secure transmission (MST) antenna. The first antenna 450 may, for example, perform short-range communication with an external device, wirelessly transmit and receive power required for charging, and transmit short-range communication signal or a electromagnetic signal including payment data. In another embodiment, an antenna structure may be formed by at least a portion of the side bezel structure 206 and/or a part of the support member 460 or a combination thereof.

The second antenna 455 may be disposed between the printed circuit board 480 and the rear plate 207. The second antenna 455 may include, for example, a near field communication (NFC) antenna, a wireless charging antenna, and/or a magnetic secure transmission (MST) antenna. For example, the second antenna 455 may perform short-range communication with an external device, wirelessly transmit and receive power required for charging, and may transmit a short-range communication signal or a electromagnetic signal including payment data. In another embodiment, an antenna structure may be formed by at least a portion of the side bezel structure 206 and/or a part of the rear plate 207 or a combination thereof.

The sealing member 490 may be positioned between the side bezel structure 206 and the rear plate 207. The sealing member 490 may be configured to block moisture and foreign material flowing into the space surrounded by the side bezel structure 206 and the rear plate 207 from the outside.

Figure 5:
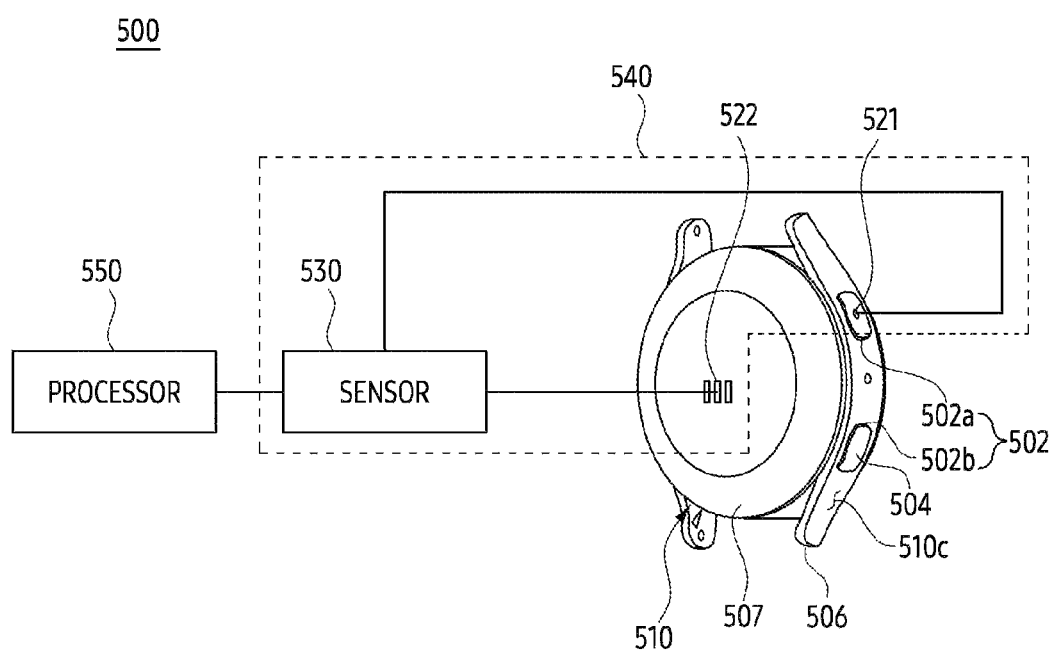
FIG. 5 illustrates an example of an electronic device according to an embodiment.

FIG. 5 illustrates an example of an electronic device according to an embodiment.

Referring to FIG. 5, the electronic device 500 (e.g., the electronic device 101 in FIG. 1 and the electronic device 200 in FIG. 2) may comprise a housing 510 (e.g., the housing 210 in FIG. 2), key buttons 503 and 504, a sensor module 540, and a processor 550 (e.g., the processor 120 in FIG. 1). The rear surface 510B, the side surface 510C, the side bezel structure 506, the rear plate 507 and/or the key buttons 503 and 504 in FIG. 5 may be substantially the same as the rear surface 210B, the side surface 210C, the side bezel structure 206, the rear plate 207, and/or the key buttons 203 and 204 in FIGS. 2, 3, and/or 4, respectively, so overlapping descriptions will be omitted.

According to an embodiment, the housing 510 may comprise a front surface (e.g., the front surface 210A in FIG. 2), the rear surface 510B, and the side surface 510C disposed between the front surface 210A and the rear surface 510B. The housing 510 may provide an inner space surrounded by the front surface 210A, the rear surface 510B, and the side surface 510C. An inner component of the electronic device 500 may be disposed in the inner space. For example, a printed circuit board (e.g., the printed circuit board 480 in FIG. 4) may be disposed in the inner space surrounded by the front surface 210A, the rear surface 510B, and the side surface 510C of the housing 510.

According to an embodiment, at least one opening 502 may be disposed on the side surface 510C of the housing 510. For example, at least one opening 502 may be formed in the side bezel structure 506 disposed on the side surface 510C of the housing 510. At least one opening 502 may penetrate the side bezel structure 506 of the housing 510. For example, at least one opening 502 may extend from an inner space surrounded by the front surface 510A, the rear surface 510B, and the side surface 510C of the housing 510 to the outer surface of the side bezel structure 506.

According to an embodiment, the key buttons 503 and 504 may be disposed on the side surface 510C of the housing 510. At least a part of the key buttons 503 and 504 may be inserted into at least one opening 502 formed on the side surface 510C. For example, a part of the body of the key buttons 503 and 504 may protrude toward the outside of the electronic device 500 through at least one opening 502 and may be visible from the outside, and the rest of the body of the key buttons 503 and 504 may be disposed in the inner space of the housing 510. According to an embodiment, the key buttons 503 and 504 may move in the inner direction of the electronic device 500 as they are pressed. For example, the key buttons 503 and 504 may comprise a first key button 503 and a second key button 504. The first key button 503 may be supported by a first opening 502a and/or an inner structure (not illustrated) of at least one opening 502 formed in the side bezel structure 506. When the first key button 503 is pressed, the first key button 503 may move to the inside of the electronic device 500 and be supported by a support member (e.g., the support member 460 in FIG. 4) disposed inside the housing 510. The second key button 504 may be supported and fixed by a second opening 502b and/or the inner structure (not illustrated) of at least one opening 502 formed in the side bezel structure 506. According to an embodiment, the first key button 503 and/or the second key button 504 moved to the inside may be pressed by an elastic body (not illustrated) disposed between the key buttons 503 and 504 and the support member 460. For example, when the external force pressing the first key button 503 is removed, the first key button 503 may move to the position before the external force is applied by the elastic body.

According to an embodiment, at least one electrode 520 may be disposed on the electronic device 500. For example, the electrode 520 may be disposed on the inner component of the electronic device 500 (e.g., the printed circuit board 480 in FIG. 4) or an outer surface of the housing 510.

According to an embodiment, the first electrode 521 may be disposed on at least one of the key buttons 503 and 504, and the second electrode 522 may be disposed on the rear plate 507. The electrodes 521 and 522 may be configured to obtain information related to the external object through contact with the external object. For example, the first key button 503 may comprise the first electrode 521. At least a part of the first key button 503 may be formed of a conductive member. The second electrode 522 may be disposed on the rear plate 507, and at least a part of the second electrode 522 may be visually exposed to the outside. The electrodes 521 and 522 may be in contact with a part of the user's body of the electronic device 500. For example, the electronic device 500 may be contacted while surrounding a part of the user's body by a binding member (e.g., the binding members 250 and 260 in FIG. 2). The rear plate 507 of the electronic device 500 may be in contact with a part of the user's body. For example, the first key button 503 or the first electrode 521 included in the first key button 503 may be in contact with the external object (e.g., a part of the user's body). The second electrode 522 may be in contact with another external object (e.g., another part of the user's body) distinct from the external object. For example, the first key button 503 may be in contact with one of the user's fingers. The second electrode 522 exposed from the rear plate 507 may be in contact with a part of the user's wrist. The electrodes 521 and 522 may be configured to transmit an electrical signal corresponding to the user's biometric signal (e.g., electrocardiogram, body temperature, blood pressure) to an electronic component (e.g., the sensor 530) disposed inside the electronic device 500 according to contact with a part of the user's body.

According to an embodiment, the sensor 530 may be disposed in the inner space of the housing 510 of the electronic device 500. For example, the sensor 530 may be disposed on one surface of the printed circuit board 480 disposed in the inner space of the housing 510.

According to an embodiment, the sensor 530 may be electrically connected to the electrodes 521 and 522. The sensor 530 may detect or identify the electrical signals transmitted from the external object (e.g., the user's body or the external electronic device) to the electrodes 521 and 522. For example, the sensor 530 may be a bio sensor. The first electrode 521 may be disposed on at least one of the key buttons 503 and 504 disposed on the side surface 510C of the electronic device 500. The sensor 530 may be electrically connected to the first electrode 521. The second electrode 522 may be disposed on the rear plate 507 disposed on the rear surface 510B of the electronic device 500. The sensor 530 may be electrically connected to the second electrode 522. A part of the user's body of the electronic device 500 may be in contact with the first electrode 521 disposed on the first key button 503. The other part of the user's body may be in contact with the second electrode 522 disposed on the rear plate 507. The other part of the user's body of the electronic device 500 may be in contact with the first electrode 521 disposed on the key buttons 503 and 504. Information related to current flowing through the user's body of the electronic device 500 may be transmitted to the sensor 530 through the electrodes 521 and 522. The sensor 530 may detect or identify the transmitted signal.

According to an embodiment, the sensor module 540 (e.g., the sensor module 176 in FIG. 1 or the sensor module 211 in FIG. 2) may comprise the first electrode 521, the second electrode 522, and the sensor 530. The sensor module 540 may sense an external environmental state (e.g., a user's physical state) and may generate the electrical signal or data value corresponding to the sensed state. For example, the sensor 530 included in the sensor module 540 of the electronic device 500 may be a biometric sensor. The first electrode 521 may be disposed on the first key button 503, and the second electrode 522 may be disposed on the rear plate 507 disposed on the rear surface 510B of the electronic device 500. The sensor 530 may be electrically connected to the first electrode 521 and the second electrode 522. The sensor 530, the first electrode 521, and the second electrode 522 may configure a biometric sensor module (e.g., an HRM sensor). A part of the user's body of the electronic device 500 may generate a micro signal (e.g., microcurrent due to heartbeat). Since the second electrode 522 is in contact with a part of the user's body, the micro signal may be sensed and transmitted to the sensor 530. The micro signal may be converted into the electrical signal or the data value through the biometric sensor module.

According to an embodiment, the processor 550 may be disposed inside the housing 510 of the electronic device 500. The processor 550 may be electrically connected to the sensor 530. For example, the processor 550 may be disposed on one surface of the printed circuit board 480 inside the housing 510 in which the sensor 530 is disposed. The processor 550 may receive sensing data sensed by the sensor 530 through a PCB transmission line (e.g., a strip transmission line or a micro strip transmission line) disposed on the printed circuit board 480.

According to an embodiment, the processor 550 may be a bio processor. The processor 120 may be configured to obtain data related to the microcurrent generated by the external object through the sensor 530 based on identifying the contact of the external object with each of the first electrode 521 and the second electrode 522. For example, the sensor 530 may be the biometric sensor. The external object may be a part of the user's body of the electronic device 500. For example, the external object may be a part of a user's finger in contact with the first electrode 521 or a user's wrist in contact with the second electrode 522.

According to an embodiment, the processor 550 may perform data processing or computation related to the user's body by receiving user's biometric information or biometric signals obtained from the sensor module 540 including the sensor 530, the first electrode 521, and the second electrode 522. For example, the processor 550 may control at least one other component (e.g., biometric information software) of the electronic device 500 connected to the processor 550 based on the biometric information or the biometric signals provided from the sensor module 540 to provide physical information to the user through the display unit (e.g., the display module 160 in FIG. 1 and the display 220 in FIG. 3). The processor 550 may process commands or data received from the sensor module 540 as at least a part of data processing or calculation, and may provide the result data to the user.

According to the above-described embodiment, the electronic device 500 may provide body-related information to the user by including a sensor module 540 that senses user-related information or signals, and a processor 550 that performs calculation and processing data obtained from the sensor module 540.

Figure 6:
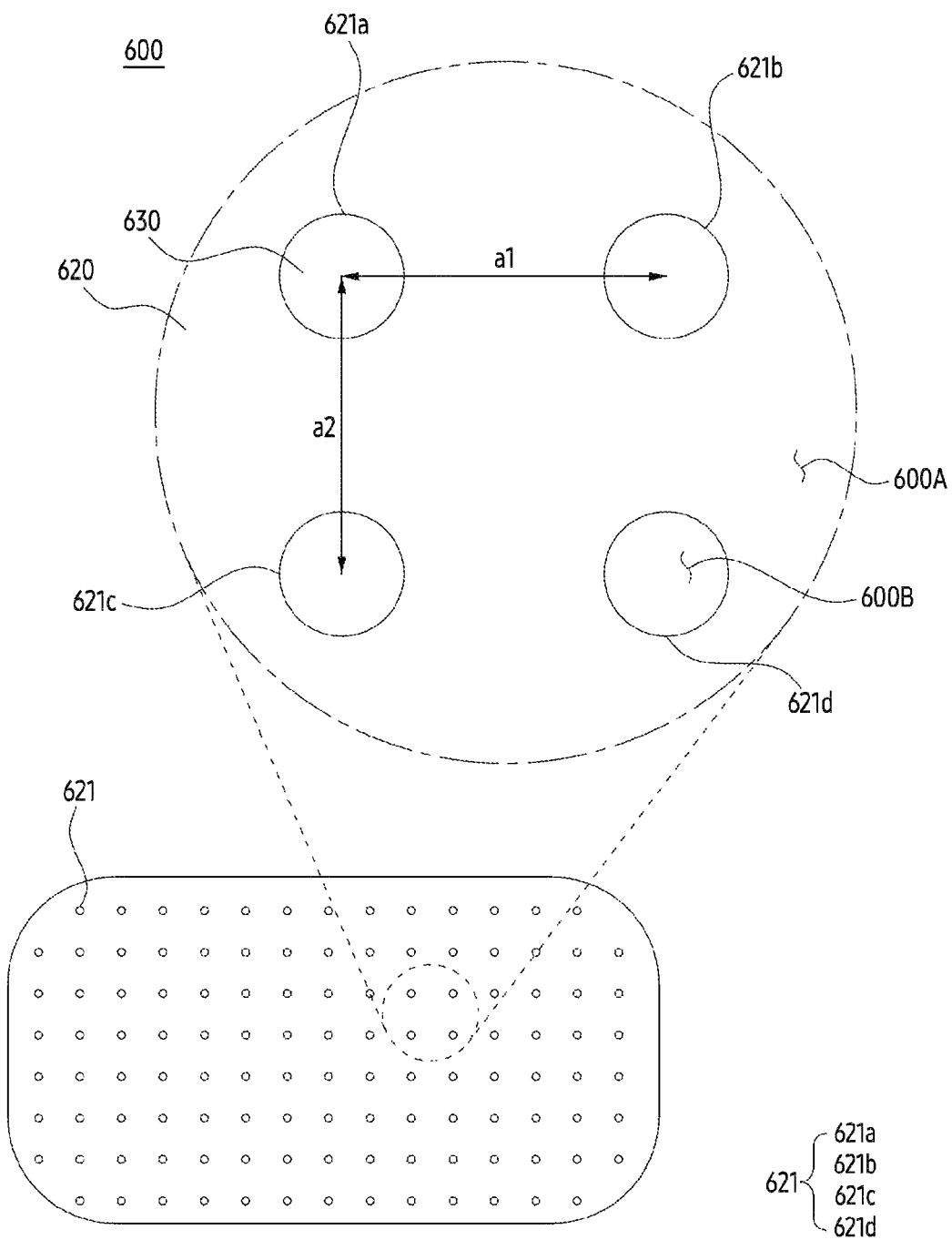
FIG. 6 is an enlarged top plan view of an enlarged key button of an electronic device according to an embodiment.
Figure 7:
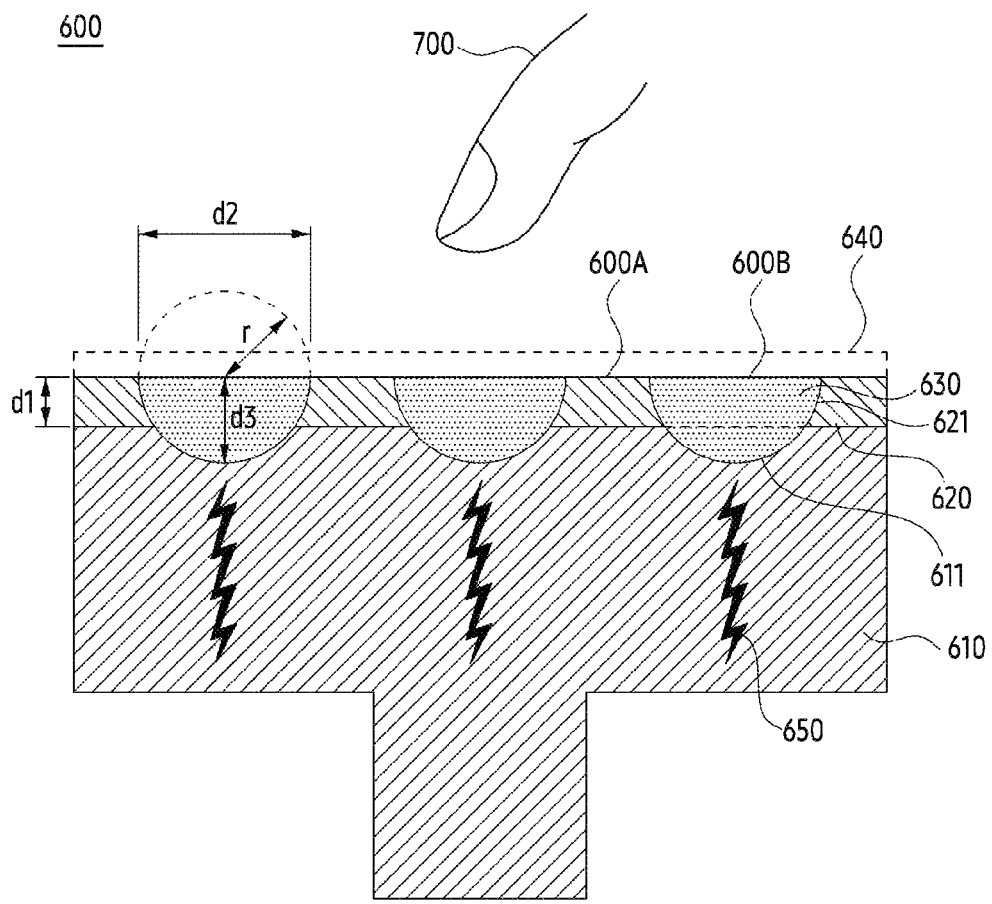
FIGS. 7 and 8 are cross-sectional views of key buttons of an electronic device according to an embodiment.
Figure 8:
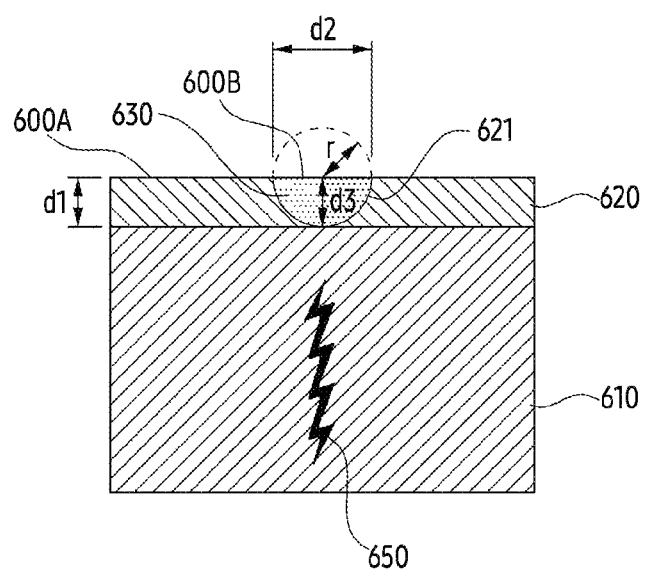

FIG. 6 is an enlarged top plan view of an enlarged key button of an electronic device according to an embodiment. FIGS. 7 and 8 are cross-sectional views of key buttons of an electronic device according to an embodiment.

Referring to FIGS. 6 and 7, the key buttons 600 (e.g., the key buttons 203, 204 in FIG. 2 and the key buttons 503, 504 in FIG. 5) included in the electronic devices (e.g., the electronic device 101 in FIG. 1, the electronic device 200 in FIG. 2, and the electronic devices 500 in FIG. 5) may comprise the metal layer 610, the deposited layer 620, and the conductive material 630.

According to an embodiment, at least a part of the key button 600 may be exposed to the outside of the electronic device 500. For example, the key button 600 may be inserted into at least one opening (e.g., at least one opening 502 in FIG. 5) of the electronic device 500. A part of the key button 600 may be exposed to the outside through the opening 502 of the electronic device 500. The rest of the key buttons 600 may be disposed inside the electronic device 500. A part of the key button 600 exposed to the outside of the electronic device 500 may be in contact with a part of the user's body.

According to an embodiment, the metal layer 610 may be a base material of the key button 600. The key button 600 including the metal layer 610 may be disposed in the opening 502 of the housing 510. The metal layer 610 may be an electrode (e.g., the first electrode 521 in FIG. 5) of the sensor (e.g., the sensor 530 in FIG. 5). The housing of the electronic device 500 (e.g., the housing 210 in FIG. 2, the housing 510 in FIG. 5) may comprise at least one of stainless used steel (SUS), aluminum, titanium, zirconium, or alloy thereof. The metal layer 610 may comprise the same material as the housing 510. For example, the metal layer 610 may comprise SUS or aluminum.

According to an embodiment, the metal layer 610 may comprise a part where the key button 600 is connected to an inner component of the electronic device 500 (e.g., the printed circuit board 480 in FIG. 4). The metal layer 610 may transmit an electrical signal transmitted from the outside of the key button 600 to the inner component (e.g., the sensor 530 in FIG. 5) of the electronic device 500. For example, a part of the key button 600 may be exposed to the outside of the electronic device 500. Through the metal layer 610 of the key button 600, the electrical signal transmitted from an external object may be transmitted to an electronic component disposed inside the electronic device 500. For example, the metal layer 610 may be electrically connected to the inner component (e.g., the sensor 530 in FIG. 5) of the electronic device 500. The metal layer 610 may transmit the electrical signal transmitted from the outside to the inner component of the electronic device 500.

According to an embodiment, the deposited layer 620 may be disposed on the metal layer 610. The deposited layer 620 may be disposed on a surface facing the outside of the key button 600. The deposited layer 620 may protect the metal layer 610 by forming a film on the metal layer 610. One surface of the deposited layer 620 facing the outside of the electronic device 500 may be discontinuous due to the grain boundary of the deposited material. For example, the deposited layer 620 may be deposited on the metal layer 610 by a physical vapor deposition (PVD) process or a chemical vapor deposition (CVD) process. Due to the thickness of the deposited layer 620 and/or the discontinuous shape of one surface, it may be difficult to transmit the electrical signal through the key button 600 from the outside. The deposited layer 620 may be formed by attaching deposited particles on the metal layer 610. For example, the deposited layer 620 may be formed through the PVD process such as evaporation or sputtering of the deposited material and/or the CVD process by a chemical reaction of the deposited material. The deposited particles configuring the deposited material may be discontinuously stacked on the metal layer 610 to form a particle boundary surface, respectively.

According to an embodiment, the deposited layer 620 may provide various colors to the key button 600. For example, the color of the metal layer 610 may be different from the color of the housing (e.g., the housing 210 in FIG. 2 and the housing 510 in FIG. 5) of the electronic device 500. The deposited layer 620 may have the same or similar color as the housing 510. As the deposited layer 620 is disposed on the metal layer 610, the key button 600 may have the same or similar color as the housing 510 to provide a unified color or metal texture of the electronic device 500. Based on the specified color, the material or thickness of the deposited layer 620 may be defined. The deposited layer 620 thickened for implementing the specified color may have high electrical resistance. Through the high resistance of the deposited layer 620, the loss of the electrical signal transmitted to the metal layer 610 through the deposited layer 620 may increase.

According to an embodiment, the deposited layer 620 may comprise at least one of titanium, chromium tungsten, silicon, aluminum, gold, copper, silver, and oxides, nitrides, carbides, and carbon nitrides thereof. The deposited layer 620 may comprise at least one of a metal material (e.g., titanium, tungsten, silicon, aluminum, gold, copper, silver), a non-metal material (e.g., nitrogen, oxygen, carbon), and a combination of a metal material and a non-metal material. For example, the combination of the metal material and the non-metal material may comprise at least one of the oxide of the metal material, the nitride of the metal material, and the carbide of the metal material. With any one or a combination of two or more of the deposited materials, the deposited layer 620 may implement various colors. According to an embodiment, the thickness of the deposited layer 620 may be 1 μm or more and 10 μm or less.

According to an embodiment, the metal layer 610 may comprise at least one groove 611. At least one groove 611 may be formed on one surface on which the metal layer 610 faces the deposited layer 620. The metal layer 610 may be in contact with the conductive material 630 occupying the at least one groove 611. At least one groove 611 may provide contact between the metal layer 610 and the conductive material 630. The at least one groove 611 may increase the contact area, thereby increasing the conductivity of the metal layer 610. For example, since a part of the metal layer 610 facing the outside where the groove 611 is formed has a curved shape, the contact area with the conductive material 630 may be increased compared to the case of having a planar shape. As the contact area increases, the conductivity of the electrical signal transmitted to the metal layer 610 through the conductive material 630 may increase.

According to an embodiment, the deposited layer 620 may comprise at least one hole 621. At least one hole 621 may penetrate the deposited layer 620. The deposited layer 620 may form a part of an outer surface of the key button 600. For example, the deposited layer 620 may be disposed on one surface on which the metal layer 610 faces the outside of the key button 600. At least one hole 621 may extend from one surface facing the outside of the deposited layer 620 to one surface that contacts with the metal layer 610 of the deposited layer 620.

According to an embodiment, a radius d2/2 of one side facing the outside of the at least one hole 621 may be greater than or equal to the thickness d1 of the deposited layer 620. For example, a laser may be point irradiated on one surface of the deposited layer 620 facing the outside to form a hemispherical hole 621. The radius d2/2 of the hemisphere may be the same as the thickness d1 of the deposited layer 620. For example, at least one hole 621 may be formed on one surface of the deposited layer 620 facing the outside through wet etching. The hole 621 may have another shape (e.g., a cylindrical shape or a conical shape) other than the hemispherical shape. On one surface of the deposited layer 620, the remaining area except for the area corresponding to at least one hole 621 may be masked. At least the one hole 621 may be formed through the wet etching on one surface of the deposited layer 620 except for the remaining masked area. A diameter d2 of one surface facing the outside of the hole 621 formed by the wet etching may be greater than the thickness d1 of the deposited layer 620. For example, the diameter d2 of one surface facing the outside of the hole 621 formed by pressing a protrusion having a diameter greater than the thickness d1 of the deposited layer 620 on one surface of the deposited layer 620 facing the outside may be greater than the thickness d1 of the deposited layer 620.

According to an embodiment, each of the at least one hole 621 may have substantially the same or similar shape as each other. For example, by irradiating the laser onto the deposited layer 620, the deposited layer 620 may comprise a plurality of holes 621a, 621b, 621c, and 621d. The size and/or depth of the shape of the plurality of holes 621a, 621b, 621c, and 621d may be constantly adjusted according to the pulse duration of the laser. The laser may be point irradiated. One surface of each of the plurality of holes 621a, 621b, 621c, and 621d facing the outside may be circular with a constant diameter due to the point irradiation. Since each of the plurality of holes 621a, 621b, 621c, and 621d has substantially the same diameter, each of the plurality of holes 621a, 621b, 621c, and 621d may have substantially the same or similar shapes.

According to an embodiment, each of the at least one hole 621 may be spaced apart at a specified interval. For example, the plurality of holes 621a, 621b, 621c, and 621d may be formed in the deposited layer 620 to have constant intervals, respectively. The interval a1 between the first hole 621a and the second hole 621b arranged in a row in the long side direction of the key button 600 may be constant. The interval a2 between the first hole 621a and the third hole 621c arranged in a row in the short side direction of the key button 600 may be constant. For example, a masking area except for an area corresponding to the plurality of holes 621a, 621b, 621c, and 621d having a specified interval may be set on one surface of the deposited layer 620 facing the outside, and the plurality of holes 621a, 621b, 621c, and 621d may be formed through wet etching. For example, the laser device, onto the deposited layer 620, may irradiate the laser at a specified interval a1 in the long side direction of the key button 600, and may irradiate the laser at a specified interval a2 in the short side direction of the key button 600. By adjusting the intervals a1 and a2, the number of at least one hole 621 formed on the deposited layer 620 may be adjusted.

According to an embodiment, the metal layer 610 may comprise a groove 611 connected to at least one hole 621 formed in the deposited layer 620. The conductive material 630 may occupy the hole 621 and the groove 611. For example, the deposited layer 620 may be disposed on the metal layer 610, and the laser may be irradiated to the deposited layer 620. The laser may form at least one hole 621 in the deposited layer 620, and a groove 611 on the metal layer 610 connected to the at least one hole 621, by penetrating the deposition layer 620 by dotted irradiation. The shape of the at least one hole 621 and the at least one groove 611 connected to the hole 621 may be a hemispherical shape. The radius r of the hemisphere may be the same as the radius of one side facing the outside of the hole 621. As the laser is point irradiated, the diameter 2r of the hemisphere may decrease. By disposing the small-diameter conductive material 630 in the hole 621 and the groove 611, a visibility difference between the conductive material 630 and the deposited layer 620 may be decrease.

According to an embodiment, the conductive material 630 may be disposed in at least one hole 621 of the deposited layer 620 and in the groove 611 of the metal layer 610. The conductive material 630 may occupy the hole 621 and the groove 611 and may be in contact with a part of the metal layer 610. The conductive material 630 may include the second surface 600B continuous with the first surface 600A of the deposited layer 620 exposed to the outside. For example, the deposited layer 620 may comprise the first surface 600A exposed to the outside. The conductive material 630 may occupy at least one hole 621 formed in the deposited layer 620. The conductive material 630 may be exposed through a surface facing the outside of the at least one hole 621. The second surface 600B of the conductive material 630 may correspond to a surface facing the outside of the at least one hole 621.

According to an embodiment, the metal layer 610 may comprise at least one groove 611 connected to at least one hole 621 formed in the deposited layer 620. A connected shape of the groove 611 and the hole 621 in which the conductive material 630 is disposed may be the hemispherical shape. A distance d3 from the metal layer 610 to the second surface 600B of the conductive material 630 may be the same as the radius d2/2 facing the outside of the hole 621. According to an embodiment, in case that the conductive material 630 is not the hemispherical shape, the distance d3 from the metal layer 610 to the second surface 600B of the conductive material 630 may be shorter than the radius d2/2 facing the outside of the hole 621. According to an embodiment, the distance d3 from the metal layer 610 to the second surface 600B exposed to the outside may be greater than the radius d2/2 of one side facing the outside of the hole 621 and may be smaller than the diameter d2 of the one surface.

According to an embodiment, the second surface 600B of the conductive material 630 and the first surface 600A of the deposited layer 620 may be continuous. The deposited layer 620 and the conductive material 630 exposed through the hole 621 may form a part of the outer surface of the key button 600. The second surface 600B may be continuous with the first surface 600A of the deposited layer 620. In case that a user touches the key button 600, the key button 600 providing a continuous outer surface may provide a soft sense of touch to the user of the electronic device 500.

According to an embodiment, the conductive material 630 may be configured to transmit the microcurrent 650 caused by the contact of the external object 700 to the metal layer 610. For example, the microcurrent 650 caused by the contact with the external object 700 may be transmitted to the metal layer 610 through the conductive material 630 penetrating the deposited layer 620. As the external object 700 (e.g., a user's finger) contacts at least a part of the second surface 600B of the outer surface of the key button formed by the first surface 600A and the second surface 600B, the microcurrent 650 may be generated. The conductive material 630 may transmit the microcurrent 650 generated by the external object 700 to the metal layer 610 in contact with the conductive material 630 through the second surface 600B.

According to an embodiment, the conductive material 630 may comprise at least one of a metal, a transparent electrode, and carbon. The conductive material 630 may comprise one of nickel, copper-tin alloy, copper-tin-zinc alloy, chromium, gold, platinum, silver, copper, tin, zinc, rhodium, ruthenium, palladium, or a combination thereof. At least one or a combination of two or more materials that may be included in the conductive material 630 may provide a color substantially the same as or similar to the color of the deposited layer 620. The key button 600 having the color provided by the deposited layer 620 may provide the same as or similar color to the color of the housing (e.g., the housing 510 in FIG. 5).

According to an embodiment, the key button 600 may further include an anti-fingerprint layer 640 disposed on the outer surface of the key button 600. For example, the anti-fingerprint layer 640 may be disposed on a continuous surface configured with the first surface 600A and the second surface 600B. The anti-fingerprint layer 640 may reduce traces generated by the external object 700 on the continuous surface by the external object 700 (e.g., the user's finger).

According to an embodiment, the equivalent resistance between the deposited layer 620 and the conductive material 630 may be 1KΩ or less. A part of the user's body may generate the microcurrent 650 at a level of 40 μA to 60 μA. Since the equivalent resistance between the deposited layer 620 and the conductive material 630 is 1KΩ or less, the microcurrent 650 generated through a part of the user's body may be transmitted to the inner component of the electronic device 500 (e.g., the sensor 530 in FIG. 4) through the deposited layer 620 and/or the conductive material 630.

Referring to FIG. 8, the key button 600 may comprise the metal layer 610, the deposited layer 620, and the conductive material 630, and at least one hole 621 included in the deposited layer 620 may be in contact with one surface facing the outside of the metal layer 610.

Unlike the conductive material in FIG. 7, the distance d3 from the metal layer 610, which is a thickness of the conductive material 630, to the second surface 600B of the conductive material 630 exposed to the outside may be the same as the thickness d1 of the deposited layer 620.

According to an embodiment, the microcurrent 650 generated by the external object may be transmitted to the metal layer 610 through the conductive material 630. The deposited layer 620 may comprise at least one hole 621 in which the conductive material 630 may be disposed in order to transmit the microcurrent 650 generated by contact with the external object to the metal layer. The conductive material 630 may be in contact with the metal layer 610 by at least one hole 621. The second surface 600B of the conductive material 630 may be exposed to the first surface 600A of the deposited layer 620 through the hole 621. The distance d3, which is the thickness of the conductive material 630, may be the same as the thickness d1 of the deposited layer 620. According to an embodiment, the shape of at least one hole 621 included in the deposited layer 620 may be the hemispherical shape. The radius r of the hemisphere may be the same as the radius d2/2 of one side facing the outside of the hole 621. For example, the deposited layer 620 may be disposed on the metal layer 610, and the laser may be irradiated from the outside of the deposited layer 620. The laser may be point irradiated and penetrate the deposited layer 620. The shape of the hole 621 corresponding to a part of the deposited layer 620 removed by the laser may be the hemispherical shape.

According to an embodiment, the conductive material 630 may be in contact with the metal layer 610 through at least one hole 621 included in the deposited layer 620. The distance d3 from the metal layer 610 of the conductive material 630 to the second surface 600B exposed to the outside may be the same as the radius d2/2 of one side facing the outside of the hole 621. For example, the conductive material 630 may be the hemispherical shape corresponding to the hole 621. The diameter 2r of the hemisphere may be the same as the diameter d2 of one surface facing the outside of the hole 621. In the conductive material 630, the distance d3 from the metal layer 610 in contact with the conductive material 630 to the second surface 600B exposed to the outside may be the same as the radius r of the hemisphere.

According to an embodiment, the conductive material 630 in FIGS. 7 and/or 8 is described as having a hemispherical shape, but is not limited thereto. For example, at least one hole 621 and/or groove 611 may comprise a part of shape of a cylinder extending from the hole 621 with the same diameter. The groove 611 in contact with the hole 621 forming a conical shape may comprise a conical corner shape. For example, the depth of the hole 621 may be smaller than the radius r of the circle corresponding to the cross-section of the hole 621 or the shape of the surface of the hole 621 facing the outside.

According to an embodiment, the conductive material 630 may be configured to transmit the microcurrent 650 generated by the contact of the external object 700 to the metal layer 610. For example, a part of the metal layer 610 may be in contact with at least one hole 621 included in the deposited layer 620 disposed on the metal layer 610. The conductive material 630 having the second surface 600B in contact with the metal layer 610 and facing the outside may be disposed in the hole 621. The second surface 600B may correspond to one surface facing the outside of the hole 621. Since one surface facing the outside of the hole 621 and the first surface 600A of the deposited layer 620 are continuous, the first surface 600A and the second surface 600B may configure continuous surfaces. As the external object 700 (e.g., a user's finger) contacts at least a part of the second surface 600B included in the continuous surface, the microcurrent 650 may be generated. The conductive material 630 may transmit the microcurrent 650 generated by the external object 700 to the metal layer 610 in contact with the conductive material 630 through the second surface 600B.

According to the above-described embodiment, the key button 600 included in the electronic device 500 includes the deposited layer 620 disposed on the metal layer 610, and thus has the same or similar color as the housing 510 of the electronic device 500, thereby providing a unified color or metal texture of the electronic device 500. The deposited layer 620 may expose the conductive material 630 to the outside by providing at least one hole 621 so that the conductive material 630 may contact the metal layer 610. The conductive material 630 exposed to the outside transmits the electrical signal transmitted by directly contacting the external object 700 to the metal layer 610, thereby reducing the loss of the electrical signal. The at least one hole 621 may comprise a plurality of holes 621a, 621b, 621c, and 621d spaced at a specified interval, thereby reducing a sense of difference with the color of the exposed conductive material 630.

Figure 9:
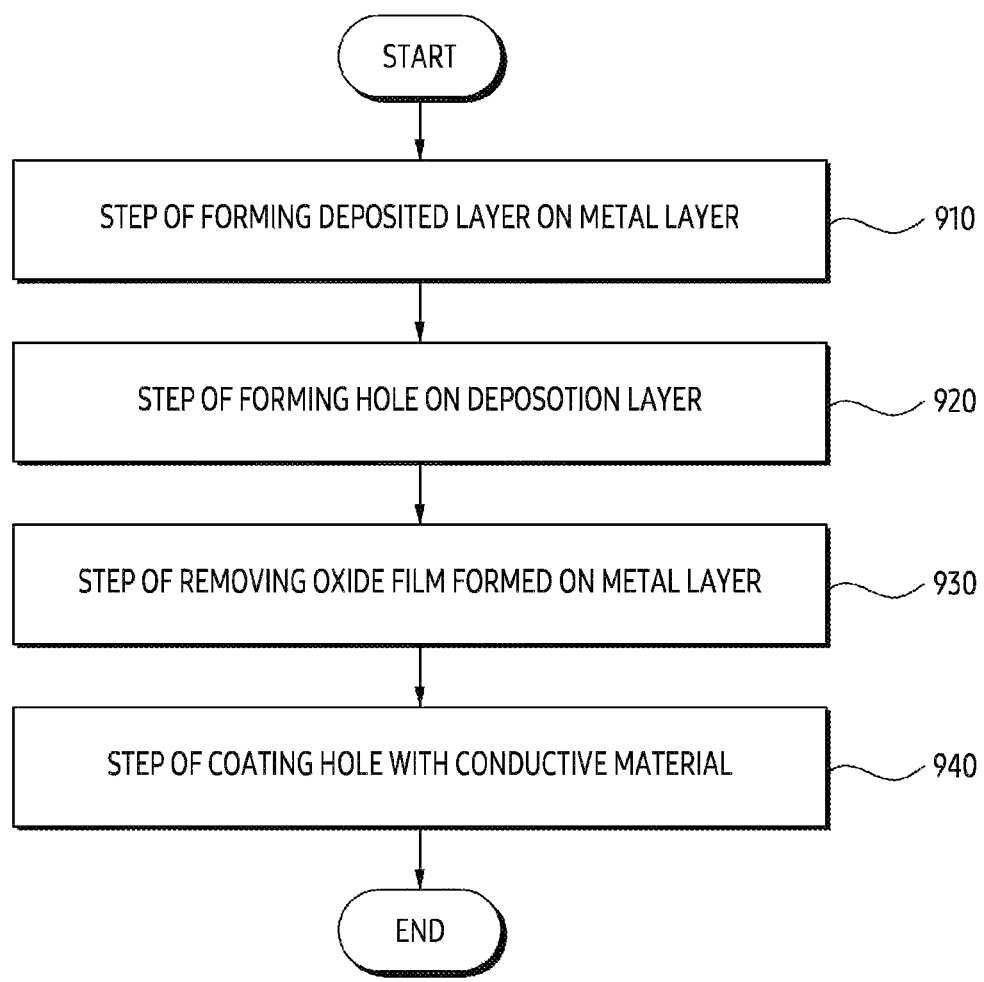
FIG. 9 is a flowchart illustrating a deposition and plating process of a key button of an electronic device.

FIG. 9 is a flowchart illustrating a deposition and plating process of a key button of an electronic device.

Referring to FIG. 9, the electronic device (e.g., the electronic device 101 in FIG. 1), the electronic device 200 in FIG. 2, the key buttons of the electronic device 500 in FIG. 5 (e.g., the key buttons 203 and 204 in FIG. 2), the key buttons 503, 504 in FIG. 5, and the deposition and plating process of the key button 600 in FIG. 6 may comprise a plurality of steps.

According to an embodiment, in step 910, a deposited layer (e.g., the deposited layer 620 in FIG. 7) may be formed on a metal layer (e.g., the metal layer 610 in FIG. 7). The deposited layer 620 may be formed on the metal layer 610 by a deposition process such as a PVD process and/or a CVD process. For example, the metal layer 610 may be disposed in a vacuum chamber together with a deposited material. Particles separated from the deposited material may form the deposited layer 620 on the metal layer 610. For example, the metal layer 610 may be disposed in the vacuum chamber together with the deposited material, deposited particles generated when the deposited material collides with gas ions (e.g., inert gas ions such as Ar) may form a film on the metal layer 610. The deposited particles configuring the deposited material may be discontinuously stacked on the metal layer 610 to form a particle boundary surface, respectively.

According to an embodiment, in step 920, at least one hole (e.g., the hole 621 in FIG. 7) may be formed on the deposited layer 620. The hole 621 may be formed from at least one process of laser irradiation, wet etching, or mechanical processing. For example, the laser may be point irradiated on one surface of the deposited layer 620 facing the outside, and at least one hole 621 having the hemispherical shape may be formed in the deposited layer 620. The radius of the hemisphere may be greater than or equal to the thickness of the deposited layer 620. The hemispherical hole 621 may expose a part of the metal layer 610 to the outside. For example, a masking area except for an area corresponding to one surface facing the outside of at least one hole 621 may be set on one surface of the deposited layer 620 facing the outside, and a part of the deposited layer 620 corresponding to the hole 621 may be removed through an etching solution. For example, the hole 621 may be formed by pressing a protrusion having a diameter corresponding to the diameter of one surface facing the outside of the hole 621 on one surface of the deposited layer 620 facing the outside.

According to an embodiment, in step 930, the oxide film formed on the metal layer 610 may be removed. For example, a laser having high density energy may be irradiated on one surface facing the outside of the deposited layer 620. The laser may penetrate the deposited layer 620 to heat the metal layer 610. The oxide film may be formed on the surface of the metal layer 610 that is exposed to heat and the outside according to the laser processing. For example, since the laser has high density energy and a part of the metal layer 610 is exposed to the outside through the hole 621, the oxide film may be formed in a part of the metal layer 610. The oxide film formed on the metal layer 610 may be removed by adding an acidic solution (e.g., hydrochloric acid) or a basic solution (e.g., sodium hydroxide aqueous solution) to the hole 621.

According to an embodiment, in step 940, at least one hole 621 formed in the deposited layer 620 may be coated with a conductive material (e.g., the conductive material 630 in FIG. 7). A conductive material 630 may be plated on the surface of the metal layer 610 to fill at least one hole 621 with the conductive material 630. For example, in the plating process, the conductive material 630 may be coated on a part of the metal layer 610 exposed to the outside through at least one hole 621. The metal layer 610 and the conductive material 630 may be put into an electrolyte solution. The metal layer 610 may be electrically connected to the cathode. The conductive material 630 may be electrically connected to the anode. By allowing a current to flow between the cathode and the anode, the conductive material 630 may be ionized. Since the metal layer 610 having conductivity is exposed through the at least one hole 621, the conductive material 630 may be plated into the metal layer 610 exposed by the at least one hole 621. The plating thickness of the conductive material 630 may be adjusted by adjusting the intensity of the current and/or the time at which the current flows.

According to the above-described embodiment, the key button may be used as an electrode of a sensor inside the electronic device through the conductive material disposed in the deposited layer forming the exterior of the key button. The conductive material may provide a path through which microcurrent generated by contact with an external object flows. By disposing the conductive material on the deposited layer having high resistance, the overall resistance of the key button may be lowered.

According to the above-described embodiment, an electronic device (e.g., the electronic device 200 in FIG. 2) may comprise a housing (e.g., the housing 210 in FIG. 2) including a front surface (e.g., the front surface 210A in FIG. 2), a rear surface (e.g., the rear surface 210B in FIG. 2), and a side surface (e.g., the side surface 210C in FIG. 2) disposed between the front surface and the rear surface, and providing an inner space surrounded by the front surface, the rear surface, and the side surface; a sensor (e.g., the sensor 530 in FIG. 5) disposed in the inner space; and a key button (e.g., the key buttons 203 and 204 in FIG. 2) including an electrode (e.g., the first electrode 521 in FIG. 5) electrically connected to the sensor and configured to obtain biometric information through a contact with an external object (e.g., the external object 700 in FIG. 7) through the sensor, and at least partially inserted into an opening (e.g., the opening 502 in FIG. 5) formed on the side surface. According to an embodiment, the key button may comprise a metal layer (e.g., the metal layer 610 in FIG. 7); a deposited layer (e.g., the deposited layer 620 in FIG. 7)) including a hole (e.g., the hole 621 in FIG. 7) connected to a part of the metal layer and disposed on the metal layer; and a conductive material (e.g., the conductive material 630 in FIG. 7) disposed in the hole and contact with the metal layer exposed through the hole. According to one embodiment, a diameter (e.g., the d2 in FIG. 7) of a one side of the hole facing an outside is greater than a thickness (e.g., the d1 in FIG. 7) of the deposited layer.

According to an embodiment, the metal layer may comprise a groove (e.g., the groove 611 in FIG. 7) connected to the hole, and the conductive material may occupy the hole and the groove.

According to an embodiment, a distance (e.g., the d3 in FIG. 7) from the metal layer to a surface of the conductive material exposed to the outside may be equal to a radius of the one side of the hole.

According to an embodiment, the hole may comprise a plurality of holes (e.g., the plurality of holes 621a, 621b, 621c, and 621d in FIG. 6), and each of the plurality of holes may be spaced at specified intervals (e.g., the a1 and a2 in FIG. 6).

According to an embodiment, a thickness of the deposited layer may be less than or equal to a radius of the one side of the hole.

According to an embodiment, a surface (e.g., the second surface 600B) of the conductive material exposed to the outside and one surface (e.g., the first surface 600A) of the deposited layer may be continuous, and the conductive material may be configured to transmit microcurrent (e.g., the microcurrent 650 in FIG. 7) generated by the contact of the external object to the metal layer.

According to an embodiment, the electronic device may further comprise an anti-fingerprint layer (e.g., the anti-fingerprint layer 640 in FIG. 7) disposed on an outer surface of the key button.

According to an embodiment, a thickness of the deposited layer may be 1 μm or more and 10 μm or less.

According to an embodiment, the housing may comprise at least one of stainless used steel (SUS), aluminum, titanium, zirconium, or alloy thereof; and the metal layer may comprise the same material as the housing.

According to an embodiment, the deposited layer may comprise at least one of Ti, Cr, W, Si, Al, Cu, Ag, oxides (O), nitrides (N), carbides (C), or carbon nitrides (CN).

According to an embodiment, the conductive material includes at least one of metal, a transparent electrode, or carbon.

According to an embodiment, the conductive material may comprise at least one of nickel, copper-tin alloy, copper-tin-zinc alloy, chromium, gold, platinum, silver, copper, tin, zinc, rhodium, ruthenium, or palladium.

According to an embodiment, an equivalent resistance between the deposited layer and the conductive material may be 1KΩ or less.

According to an embodiment, the electronic device may comprise another electrode (e.g., the second electrode 522 in FIG. 5) distinct from the electrode; and a processor (e.g., the processor 550 in FIG. 5). According to an embodiment, the processor may be configured to obtain data related to microcurrent generated by the external object based on identifying the contact of the external object with each of the electrode and the other electrode, through the sensor.

According to an embodiment, the sensor may comprise an ECG sensor or a fingerprint sensor.

According to an embodiment, an electronic device may comprise a housing including a front surface, a rear surface contact with a part of a user's body when the electronic device is worn by the user, and a side surface disposed between the front surface and the rear surface, and providing an inner space surrounded by the front surface, the rear surface, and the side surface; a display (e.g., the display 220 in FIG. 2) disposed on the front surface; a strap (e.g., the binding members 250 and 260 in FIG. 2) surrounding the part of the user's body when the electronic device is worn by the user and is rotatable with respect to the housing; a sensor disposed in the inner space; an at least one key button including a first electrode (e.g., the first electrode 521 in FIG. 5) electrically connected to the sensor and configured to obtain biometric information through a contact with an external object through the sensor, and at least partially inserted into an opening formed on the side surface; and a second electrode (e.g., the second electrode 522 in FIG. 5) disposed on the rear surface. According to an embodiment, the at least one key button may comprise a metal layer having a groove; a deposited layer including a hole connected to the groove and disposed on the metal layer; a conductive material disposed in the groove and the hole and contact with the metal layer exposed through the groove; and a processor. According to an embodiment, a diameter of a one side of the hole facing an outside is greater than a thickness of the deposited layer and the processor is configured to obtain data related to the biometric information based on sensing data obtained through the sensor electrically connected to the first electrode and the second electrode.

According to an embodiment, a connected shape of the groove and the hole may be a hemisphere shape, and a radius of the hemisphere may be the same as a radius of the one side of the hole.

According to an embodiment, a distance from the metal layer to a surface of the conductive material exposed to the outside may be shorter than or equal to a radius of the one side of the hole.

According to an embodiment, the hole may comprise a plurality of holes, and each of the plurality of holes are spaced at specified intervals.

According to an embodiment, a surface of the conductive material exposed to the outside and one surface of the deposited layer may be continuous, and the conductive material may be configured to transmit microcurrent generated by a contact of the external object to the metal layer. According to an embodiment, the conductive material may be plated on the surface of the metal layer so as to fill the hole with the conductive material.

According to an embodiment, the electronic device may further include an anti-fingerprint layer disposed on an outer surface of the key.

According to an embodiment, the sensor may comprise an ECG sensor or a fingerprint sensor.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:
1. A wearable electronic device comprising:
a housing including a side surface;
a sensor in the housing;
an electrode;
a processor; and
a mechanical key button partially disposed in the housing, wherein the mechanical key button includes:
a metal layer connected to the sensor,
a deposited layer disposed on the metal layer and including a hole extending to the metal layer, and
a conductive material that is at least partially disposed in the hole for contacting with the metal layer, is visible from the side surface, and is configured to transmit, through the metal layer to the sensor, a current caused by an external object contacted with the conductive material,
wherein the metal layer includes a groove extending from the hole,
wherein the conductive material is disposed in the groove and the hole,
wherein the conductive material occupies both the deposited layer and the metal layer,
wherein the processor is configured to obtain data related to the current generated by the external object based on identifying a contact of the mechanical key button with a part of the external object and a contact of the electrode with another part of the external object, through the sensor, and
wherein the part of the external object and the other part of the external object are different parts of a body of a user.

2. The wearable electronic device of claim 1, wherein a distance from the groove to a surface of the conductive material exposed to an outside of the wearable electronic device is equal to or shorter than a radius of the hole.

3. The wearable electronic device of claim 1,
wherein a thickness of the conductive material is greater than a thickness of the deposited layer.

4. The wearable electronic device of claim 1, wherein a thickness of the deposited layer is less than or equal to a radius of the hole measured across an outer surface of the mechanical key button.

5. The wearable electronic device of claim 4, wherein a surface of the conductive material exposed to the outside of the wearable electronic device and one surface of the deposited layer are continuous.

6. The wearable electronic device of claim 5, further comprising an anti-fingerprint layer disposed on the outer surface of the mechanical key button.

7. The wearable electronic device of claim 1, wherein a thickness of the deposited layer is 1 μm or more and 10 μm or less.

8. The wearable electronic device of claim 1,
wherein the housing includes at least one of stainless used steel (SUS), aluminum, titanium, zirconium, or alloy thereof, and
wherein the metal layer includes the same material as the housing.

9. The wearable electronic device of claim 1, wherein the deposited layer includes at least one of Ti, Cr, W, Si, Al, Cu, Ag, oxides (O), nitrides (N), carbides (C), or carbon nitrides (CN).

10. The wearable electronic device of claim 1, wherein the conductive material includes at least one of metal, a transparent electrode, or carbon.

11. The wearable electronic device of claim 1, wherein the conductive material includes at least one of nickel, copper-tin alloy, copper-tin-zinc alloy, chromium, gold, platinum, silver, copper, tin, zinc, rhodium, ruthenium, or palladium.

12. The wearable electronic device of claim 1, wherein an equivalent resistance between the deposited layer and the conductive material is 1KΩ or less.

13. The wearable electronic device of claim 1, wherein the sensor includes an electrocardiogram (ECG) sensor or a fingerprint sensor.

14. A wearable electronic device comprising:
a housing including a front surface, a rear surface, and a side surface disposed between the front surface and the rear surface, and providing an inner space surrounded by the front surface, the rear surface, and the side surface;
a display disposed on the front surface;
a sensor disposed in the inner space;
an electrode;
a processor; and
a mechanical key button configured to obtain biometric information through the sensor, and partially inserted into an opening formed on the side surface,
wherein the mechanical key button includes:
a metal layer including a groove and connected with the sensor,
a deposited layer disposed on the metal layer and including a hole connected to the groove, and
a conductive material that is stored in the groove and the hole, is visible from the side surface for transmit, through the metal layer to the sensor, a current caused by an external object contacted with the conductive material,
wherein the conductive material occupies both the deposited layer and the metal layer,
wherein the processor is configured to obtain data related to the current generated by the external object based on identifying a contact of the mechanical key button with a part of the external object and a contact of the electrode with another part of the external object, through the sensor, and
wherein the part of the external object and the other part of the external object are different parts of a body of a user.

15. The wearable electronic device of claim 14, wherein a distance from the groove to a surface of the conductive material exposed to an outside of the wearable electronic device is shorter than or equal to a radius of the hole.

16. The wearable electronic device of claim 14,
wherein a thickness of the conductive material is greater than a thickness of the deposited layer.

17. The wearable electronic device of claim 14,
wherein a surface of the conductive material exposed to an outside of the wearable electronic device and one surface of the deposited layer are continuous, and
wherein the hole has a concave shape.

18. The wearable electronic device of claim 14, wherein the sensor includes an electrocardiogram (ECG) sensor or a fingerprint sensor.

* * * * *